United States Patent
Maschke (10) Patent No.: US 7,729,745 B2
(45) Date of Patent: *Jun. 1, 2010

(54) DEVICE FOR CARRYING OUT ROTABLATION

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 99 days.

This patent is subject to a terminal disclaimer.

(21) Appl. No.: 11/526,249

(22) Filed: Sep. 22, 2006

(65) Prior Publication Data

US 2007/0066983 A1    Mar. 22, 2007

(30) Foreign Application Priority Data

Sep. 22, 2005    (DE) ................ 10 2005 048 892

(51) Int. Cl.
*A61B 5/05* (2006.01)

(52) U.S. Cl. ................ 600/427; 600/439; 600/471; 600/478

(58) Field of Classification Search .............. 600/407, 600/424, 427, 439, 476–480; 606/159
See application file for complete search history.

(56) References Cited

U.S. PATENT DOCUMENTS

| | | | |
|---|---|---|---|
| 4,990,134 A | 2/1991 | Auth | |
| 5,061,267 A | 10/1991 | Zeiher | |
| 5,193,546 A | 3/1993 | Shaknovich | |
| 5,287,858 A * | 2/1994 | Hammerslag et al. | 600/585 |
| 5,312,427 A | 5/1994 | Shturman | |
| 5,356,418 A | 10/1994 | Shturman | |
| 5,391,199 A | 2/1995 | Ben-Haim | |
| 5,540,959 A | 7/1996 | Wang | |
| 5,638,819 A | 6/1997 | Manwaring et al. | |
| 5,752,513 A | 5/1998 | Acker et al. | |
| 5,769,087 A * | 6/1998 | Westphal et al. | 600/573 |
| 5,827,997 A | 10/1998 | Chung et al. | |
| 5,830,145 A * | 11/1998 | Tenhoff | 600/463 |
| 5,897,529 A * | 4/1999 | Ponzi | 604/95.04 |
| 5,921,926 A | 7/1999 | Rolland et al. | |
| 6,148,095 A * | 11/2000 | Prause et al. | 382/131 |
| 6,217,527 B1 * | 4/2001 | Selmon et al. | 600/585 |
| 6,233,476 B1 | 5/2001 | Strommer et al. | |
| 6,298,261 B1 | 10/2001 | Rex | |
| 6,299,622 B1 * | 10/2001 | Snow et al. | 606/159 |
| 6,366,799 B1 | 4/2002 | Acker et al. | |

(Continued)

FOREIGN PATENT DOCUMENTS

DE    3785300 T2    5/1988

(Continued)

OTHER PUBLICATIONS

R.J. Dickinson et al., "Miniature ultrasonic probe construction for minimal access surgery", Phys. Med. Biol. 49, 2004, pp. 3527-3538.

(Continued)

*Primary Examiner*—Brian Casler
*Assistant Examiner*—Jonathan G Cwern (57) ABSTRACT

Device for carrying out rotablation, comprising a rotablation catheter, an OCT sensor, an IVUS sensor, position sensors and also an image processing unit, which is embodied for the creation of combined 2D or 3D images based on the data of the sensors.

19 Claims, 4 Drawing Sheets

U.S. PATENT DOCUMENTS

| | | |
|---|---|---|
| 6,506,972 B1 | 1/2003 | Wang |
| 6,546,271 B1 | 4/2003 | Reisfeld |
| 6,673,999 B1 | 1/2004 | Wang et al. |
| 6,713,671 B1 | 3/2004 | Wang et al. |
| 6,772,001 B2 | 8/2004 | Maschke |
| 7,280,686 B2 | 10/2007 | Hornegger et al. |
| 2001/0031919 A1 | 10/2001 | Strommer et al. |
| 2002/0019644 A1* | 2/2002 | Hastings et al. ............. 606/159 |
| 2002/0049375 A1 | 4/2002 | Strommer et al. |
| 2002/0065455 A1 | 5/2002 | Ben-Haim et al. |
| 2002/0077546 A1 | 6/2002 | Aldefeld et al. |
| 2002/0087208 A1* | 7/2002 | Koblish et al. ............. 607/113 |
| 2002/0133057 A1* | 9/2002 | Kukuk ........................ 600/101 |
| 2002/0188193 A1* | 12/2002 | Biglieri et al. ............. 600/411 |
| 2003/0080284 A1* | 5/2003 | Wake et al. ................. 250/221 |
| 2003/0195419 A1* | 10/2003 | Harada ....................... 600/437 |
| 2004/0133106 A1* | 7/2004 | Kakee et al. ................ 600/437 |
| 2005/0015006 A1* | 1/2005 | Mitschke et al. ............ 600/431 |
| 2005/0101859 A1 | 5/2005 | Maschke |
| 2005/0113685 A1 | 5/2005 | Maschke et al. |
| 2005/0203553 A1 | 9/2005 | Maschke |
| 2005/0203558 A1 | 9/2005 | Maschke |
| 2006/0015126 A1* | 1/2006 | Sher ........................... 606/159 |
| 2006/0081031 A1* | 4/2006 | Anderson et al. ............... 73/9 |

FOREIGN PATENT DOCUMENTS

| | | |
|---|---|---|
| DE | 4037586 A1 | 5/1992 |
| DE | 69514238 T2 | 6/1997 |
| DE | 19827460 A1 | 12/1998 |
| DE | 19852467 A1 | 7/1999 |
| DE | 10051244 A1 | 5/2002 |
| DE | 100 45 036 C1 | 7/2002 |
| DE | 10224011 A1 | 12/2003 |
| DE | 103 43 808 A1 | 5/2005 |
| DE | 103 54 496 A1 | 7/2005 |
| DE | 10 2004 008 368 A1 | 9/2005 |
| DE | 10 2004 008 370 A1 | 9/2005 |
| EP | 0 229 620 B1 | 7/1987 |
| EP | 0 344 279 B1 | 12/1989 |
| EP | 0993804 A1 | 4/2000 |
| EP | 1 027 088 B1 | 8/2000 |
| EP | 1034738 B1 | 9/2000 |
| EP | 1 299 044 B1 | 4/2003 |
| WO | 0111409 A2 | 2/2001 |

OTHER PUBLICATIONS

Axiom Artis dFA DynaCT, "A breakthrough in interventional 3D imaging", Siemens AG, © 2005 Siemens Medical Solutions, , Order No. A91100-M1400-D159-10-7600, Printed in Germany.

Greg Freiherr, "C-arm technology brings soft-tissue resolution to angio suite" Diagnostic Imaging, Mar. 2005, p. 57.

H. V. Bibra et al., "Kontrastechokardiographie", Zeitschrift für Kardiologie, Verlag Steinkopff, Jan. 1, 2000, pp. I/86-I/96, vol. 89, Supplement.

M.B. Nielsen et al., "Contrast enhanced ultrasound in liver imaging",European Journal of Radiology, 2004, pp. S3-S8, Elsevier Ireland Ltd.

* cited by examiner

DEVICE FOR CARRYING OUT ROTABLATION

CROSS REFERENCE TO RELATED APPLICATIONS

This application claims priority of German application No. 10 2005 048 892.7 filed Sep. 22, 2005, which is incorporated by reference herein in its entirety.

FIELD OF THE INVENTION

The invention relates to a device for carrying out rotablation.

BACKGROUND OF THE INVENTION

Diseases of the vascular vessels are among the most frequent diseases with fatal outcomes. In particular these include coronary infarction caused by diseases of the coronary vessels. If arteriosclerotic plaque causes an occlusion of coronary vessels, these symptoms are generally treated using Percutaneous Transluminal Coronary Angioplasty (PCTA). The constricted points of the coronary vessels are expanded in such cases with a balloon catheter. However clinical studies have shown that with very many patients a restenosis occurs, in some cases these types of restenosis have occurred in 50% of the patients. High-frequency rotablation angioplasty has been known as an alternative method for a number of years, which can be used advantageously, especially for fibrotic or calcified or extensive stenoses.

To reduce the danger of the formation of restenoses, coronary rotablation is used in order to achieve a recanalization of stenosized coronary arteries through "debulking". Conventional rotablation catheters consist of a diamond-tipped olive-shaped drill head which is rotated at very high speed and selectively grinds away and removes calcified and fibrotic plaque, while the stochastic vessel wall is pushed away from the drill head and accordingly not damaged. This method has become known as "differential cutting". The microparticles removed are flushed away into the periphery. Such a rotablation catheter is now seen as a valuable instrument for serious vertical lesions which cannot be removed by simple balloon angioplasty. By contrast with balloon angioplasty the restenosis is not widened. At a typical speed of rotation of 150,000 rpm the ground-off microparticles are so small that they are filtered by organs such as liver, lungs and spleen without causing damage in the body.

A device for transluminal microdissection is known from EP 0 229 620 B1. This document describes a rotablation catheter consisting of a drilling head with a diameter of around 1 to 3 mm, which is connected via a highly-flexible shaft to a pneumatically-driven turbine. The turbine is driven by compressed air and controlled from an operating device. The flexible drive shaft consists of a drive cable and is surrounded by a shell through which a flushing fluid is supplied under pressure. The flushing fluid prevents the drive cable heating up and washes out the microparticles to distal locations. This therapy is conducted under x-ray control after provision of contrast means with an angiography device. The disadvantage is however that the parts of the body to be examined, such as coronary vessels, are only shown in two dimensions as a silhouette. Thus no information can be provided about the structure of the deposit, its thickness or inflammatory processes. The medical personnel can barely distinguish between plaque and vessel wall during the intervention, since assessing the severity of the calcification and especially the position of the calcium in the plaque is difficult on the basis of the angiographic image. Accordingly the risk arises of either too little plaque being removed and the desired blood flow not being re-established, or that the risk of a restenosis remains, in extreme cases too much tissue can be removed, resulting in a perforation of the vessel.

In DE 10 2004 008 368 A1 a rotablation catheter with an IVUS sensor for use in blood vessels has been proposed. The image display in the remote area of the restenosis is improved with this catheter.

In DE 10 2004 008 370 A1 a rotablation catheter with an integrated OCT sensor for use in blood vessels has been proposed, through which the image display in the local area of the restenosis is improved.

A medical examination and treatment system has been proposed by US 2005/0101859 A1 which combines the OCT and IVUS imaging methods in one device. This enables overlaid 2D image recordings to be created, with the OCT image element being used for the local area and the IVUS image element for the remote area.

A medical examination and/or treatment system is known from US 2005/0113685 A1, in which the imaging methods OCT and IVUS are combined in one catheter, which is also provided with a position sensor. 3D images can be created by means of the information recorded by the position sensor.

The factor common to all known solutions however is that they only resolve individual problems in each case, it has not however been possible thus far to integrate the conventional catheter in an optimum way into the medical workflow.

SUMMARY OF THE INVENTION

The underlying problem addressed by the invention is that of specifying a device which is better integrated into the medical workflow and allows optimum diagnostic imaging within the framework of a minimally invasive medical therapy.

To achieve this object, provision is made for an inventive device of the type mentioned at the start to feature a rotablation catheter, an OCT sensor, an IVUS sensor, position sensors and also an image processing unit which is embodied for creation of combined 2D and/or 3D image recordings based on the data of the sensor.

The invention is based on the knowledge that previously separate known catheters are able to be combined into an integrated unit by using an IVUS sensor, an OCT sensor and also electromagnetic position sensors and the picture information obtained in this way can be overlaid in a 2D presentation used to create a 3D image recording.

The inventive device is preferably integrated into a medical treatment device, especially an x-ray device. Such an angiographic or cardiological x-ray system with high-voltage generator, x-ray source, beam diaphragm, image detector unit, patient table, emitter and detector stands and a digital imaging system makes the setting of angiographic x-ray images as well as optical images possible in the shape of computer tomography images and is able to process, present and overlay the information and recorded images supplied by the inventive device.

A magnetic control, but also alternatively a mechanical control can be provided in the inventive device, which preferably features pulling wires in order to deflect the catheter tip. In this way the tip of the catheter can be deflected to one side.

There can also be provision for controlling the catheter through an external magnetic field, in which case the catheter features at least one permanent magnet and/or at least one electromagnet. In a further embodiment of the invention the receiver coils can have iron cores and optionally be used as receive antenna or as electromagnets for magnetic navigation.

To achieve a miniaturization of the catheter it is not necessary for the coils to be arranged orthogonally in relation to each other, instead they can be disposed at any given angle, especially around 60°.

With the inventive device the OCT sensor and/or the IVUS sensor can be aligned to one side in relation to the longitudinal axis of the catheter. Accordingly the OCT sensor and the IVUS sensor can be rotated separately or together around the longitudinal axis of the catheter. Alternatively however a number of stationary sensors distributed around the circumference can be provided, which are interrogated in turn. It is also possible for the catheter to be advanced and withdrawn at a definable speed by a drive unit. In this way three-dimensional image recordings can be made.

As part of the image processing the image processing unit of the inventive device can be embodied for approximation of the center line and/or of the envelope of the part of the body to be examined, especially of a vessel. The vessel envelope can be used in further image postprocessing steps. For example, with the aid of the envelope the three-dimensional OCT-IVUS images can be registered with other anatomical image data, which originates from a 3D angiography system for example, and can subsequently be shown fused. In this case the 3D images recorded by the catheter and the anatomical image data are expediently transferred to a common coordinate system.

In order to avoid movement artifacts with the inventive device, which arise for example through breathing, the movement of the heart or other organs, the frequency and/or the amplitude of the movement can be recorded and computationally corrected.

To avoid faults in the signals recorded by the sensors, provision can be made for the sensors to be able to be read out offset in time. For example x-ray detectors and an electrocardiogram which may be present are not read out if the transmitters of the electromagnetic position system are active. The OCT sensors and the position sensors are not read out if the x-ray radiation is active. Thus only those signals are detected in each case which are not influenced by faults.

Especially good results can be obtained if the inventive device has a coating to shield it from electromagnetic fields. Such a coating can be a thin-film layer made of conducting nanoparticles.

To prevent the patient being at risk from mains voltage, the catheter and its sensors can be electrically decoupled from the mains voltage.

To facilitate locating the catheter using x-ray images, the catheter can feature x-ray markers.

To reduce the frictional resistance of the catheter while it is moving within a vessel it can be provided with a coating which preferably consists of a silicon material and/or nanomaterials. To support positioning, the catheter can have an inflatable balloon, especially at its tip.

To output a warning of high temperature if necessary, the catheter can have a temperature senor preferably arranged at its tip, and also a pressure sensor if necessary.

In addition the invention relates to a medical treatment device, especially an x-ray device. The inventive treatment device comprises a unit for carrying out rotablation of the type described.

In addition the invention relates to a method for creating examination images when carrying out rotablation. The inventive method is characterized in that a rotablation catheter is used which possesses an OCT sensor, an IVUS sensor and position sensors, in which case an image processing unit can be used to create combined 2D and/or 3D recorded images based on the data of the sensors.

BRIEF DESCRIPTION OF THE DRAWINGS

Further advantages and details of the invention are explained on the basis of exemplary embodiments which refer to the figures. The figures are schematic diagrams and show.

DETAILED DESCRIPTION OF THE INVENTION

Figure 1:
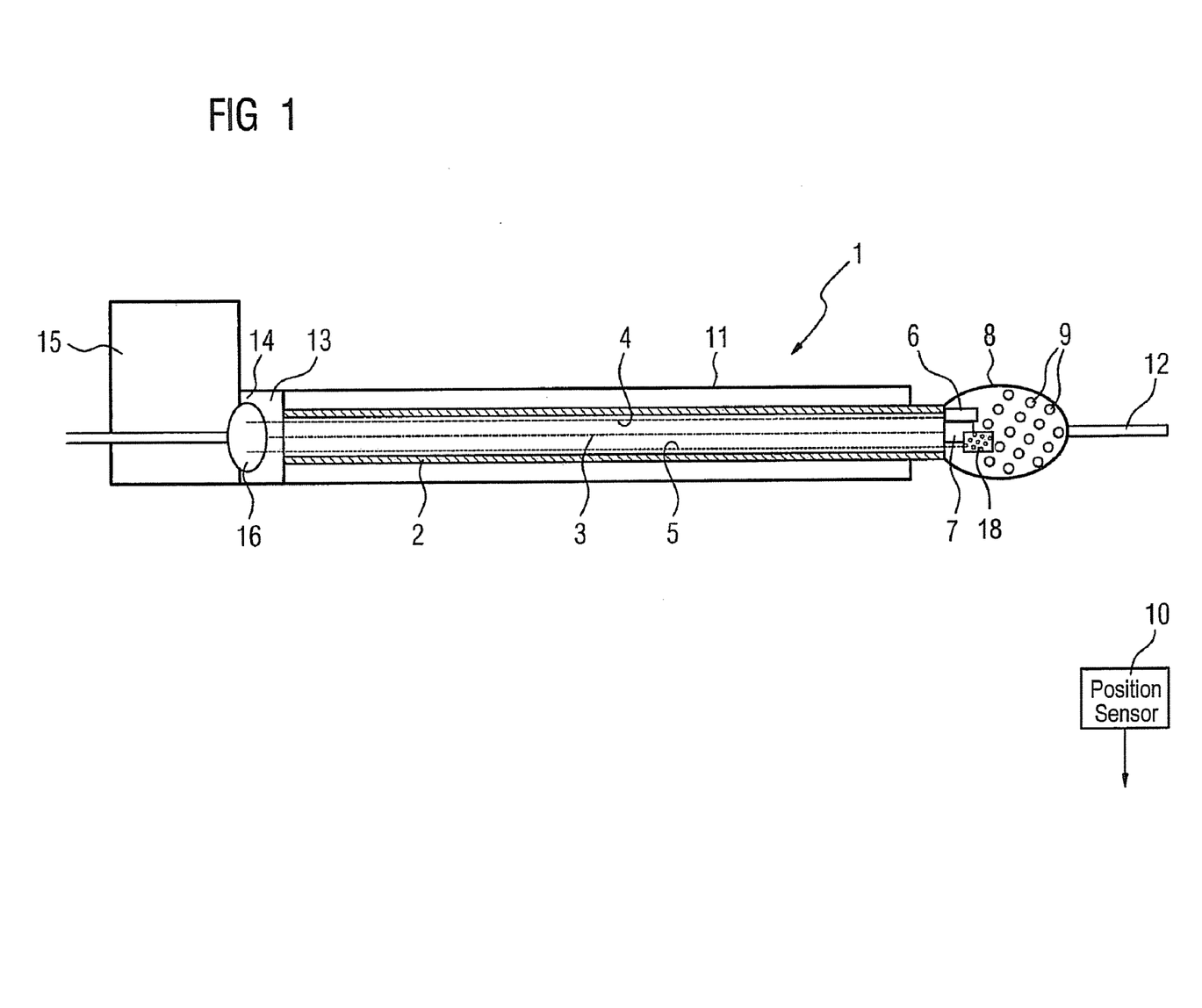
FIG. 1 an inventive device for carrying out rotablation.

FIG. 1 shows an inventive device 1 for carrying out rotablation which comprises a rotablation catheter. The device 1 features a hollow flexible drive shaft 2, into which an OCT signal line 3 and an IVUS signal line 4 are integrated. In addition a signal line 5 for a position sensor system, which is embodied as an electromagnetic sensor system, is arranged in the flexible drive shaft 2. An IVUS sensor 6 and an OCT sensor 7 are integrated into the drill head 8. On the circumference of the olive-shaped drill head are arranged grinding and cutting particles 9, through which arteriosclerotic plaque can be removed. A light exit window for the OCT sensor 7 is located on the drill head 8. Furthermore magnetic sensors 18 of the sensor system are arranged in the drill head 8. These sensors interoperate with a position sensor 10 which is arranged outside the body of the patient.

The drive shaft 2 is surrounded by a catheter sheath 11. A guide wire 12 is routed in the longitudinal direction through the device 1 and makes it possible to move and position the catheter 1 within a vessel. At the rear end of the device 1 there is a connection 13 of a mechanical connection system as well as a connection 14 for contrast means or flushing fluid.

A signal interface and a drive unit 15 are connected via a rotation coupling 16 to the device 1.

For the device 1 shown in FIG. 1 the drill head 8 for rotablation is linked to the OCT sensor 7, the IVUS sensor 6, position sensors to form an integrated device.

Figure 2:
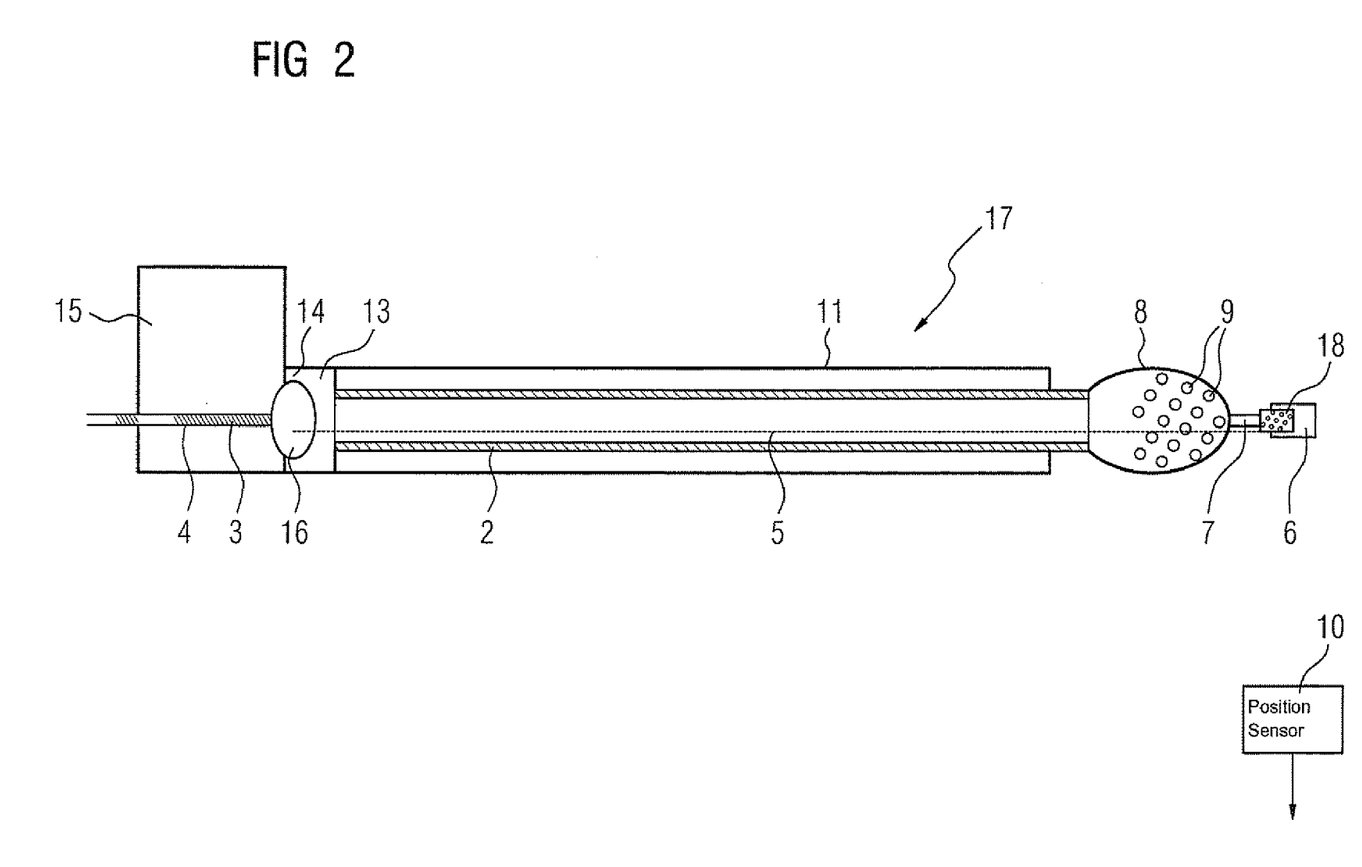
FIG. 2 a second exemplary embodiment of an inventive device for carrying out rotablation, FIG. 3 an inventive treatment unit with the device for carrying out rotablation, and FIG. 4 a schematic diagram of the sensor readout with the treatment unit shown in FIG. 3.

FIG. 2 shows a second exemplary embodiment a device for carrying out rotablation.

The same reference symbols are used for those components of the device which correspond to those shown in the first exemplary embodiment.

The device 17 shown in FIG. 2 for carrying out rotablation, as in the first exemplary embodiment, comprises a catheter with a catheter sheath 11, in which signal lines 3, 4 for IVUS and OCT are accommodated. These lines are in this case accommodated in the hollow flexible drive shaft 2, as are signal lines 5 for antennas of the position sensors. A light exit window of an OCT sensor 7 and alongside it an IVUS sensor 6 are arranged in front of the drill head 8, which is covered with grinding and cutting particles 9. In the area of the sensors 6, 7 there are magnetic sensors 18 which interoperate with an external position sensor 10.

The rear end of the device 17 comprising a catheter is constructed as in the first exemplary embodiment and includes a connection 14 for contrast means and flushing fluid, a connection of a mechanical connection system 13, a drive unit 15 with a signal interface and also a rotation coupling 16 for connecting the guide wire 12 to the catheter.

The two devices 1, 17 shown in FIGS. 1 and 2 each possess an OCT sensor and an IVUS sensor. The OCT sensor delivers especially good images of the local area, the IVUS sensor delivers a good representation of layers further away or deeper down.

The devices 1, 17 are connected to an image processing unit which creates one common image from the images delivered by the two sensors. To do this it uses a section of the image delivered by the OCT sensor for the local area and for the remote area the complementary part of the IVUS image, the two sections are registered with each other by means of the data of the position sensors and fused together into a joint image. In this way sectional images of the vessel being examined are obtained, which can be assigned precisely to a defined position in the body. Computational methods are employed to use the data of the position sensor in order to approximate the center line and the envelope of the vessel being examined. Subsequently the individual sectional images are combined to form a volume data set so that an exact and thus especially realistic image is produced.

In the approximation of the center line of the vessel and the envelope of the vessel the geometrical information of the center line is used and combined with the sensor positions recorded during imaging, which greatly reduces the artifacts in 3D imaging. The 3D co-ordinates of the center line and the sensor positions recorded during imaging are subtracted from one other. The result of the subtraction is then used for each of the recorded 2D images for exact 3D reconstruction. This envelope of the vessel can be used for further stages in processing the image. With the aid of the envelope the 3D-reconstructed OCT-IVUS images are registered with other anatomical image data such as from a 3D angiography device of the same vessel section and subsequently fused together.

The position sensors 10 used in the exemplary embodiments of FIGS. 1 and 2 are electromagnetic position sensors to create 3D OCT-IVUS images from 2D OCT-IVUS images. The recording of the orientation and position of the catheter in a three-dimensional co-ordinate system is undertaken by transmit coils in the object and receive coils in the room or conversely with receive coils in the object and transmit coils in the room.

The electromagnetic transmitter or alternatively the electromagnetic receiver can be located in the catheter. Conversely the corresponding electromagnetic receiver or transmitter can be accommodated outside the body. Normally at least one transmitter emitting radiation in the X, Y, Z direction is assigned to a receiver or conversely a receiver with X, Y, Z receive directions is assigned to a transmitter to allow for location in the room. The coils of the EMP are not arranged exclusively orthogonally to each other but at any given angle of for example 60° in order to achieve better miniaturization which makes it possible to build the position sensors into a catheter.

The image information of the catheter which is recorded with the sensors is combined or overlaid with other medical images such as 2D or 3D recordings. The OCT-IVUS images of the catheter are displayed jointly with the x-ray images. This makes the information about the images of the device and the x-ray images visible jointly for the user and makes more rapid and better diagnosis possible. In addition 2D-2D, 2D-3D, 3D-3D and 3D-4D and 4D-4D overlays are possible, in which case the angiographic x-ray images are combined in each case with the images of the device by segmentation, registration and image fusion. Images the following modalities and methods can be used for overlaying: Sonography including IVUS, radiography, fluoroscopy, angiography, OCT, discrete tomography, Positron Emission Tomography, nuclear medical diagnostics, computer tomography, nuclear resonance tomography including intracardial MR, optical recording including endoscopy, fluorescence and optical markers.

The device for carrying out rotablation is part of a medical examination unit which possesses a functional unit for rectification of movement artifacts which arise as a result of breathing and the movement of the heart and the blood vessels. To rectify the breathing artifacts a breast band can also be used which determines via the appropriate sensors the breathing amplitude and frequency so that the image processing unit can make the necessary corrective calculations in order to calculate out the movement artifacts from the image information.

To increase the location accuracy the transmit coils are operated and evaluated cyclically at specific intervals in time with different frequencies. To avoid sensor artifacts which can be produced by overlaying signals of the individual sensors it is proposed to read out the sensors offset in time and clocked. For example the x-ray detectors and the ECG are not read out if the transmitters of the electromagnetic positioning system are active. The OCT sensors and positions sensors are not read out if the x-ray radiation is active Thus only such signals are ever read out as are not subject to disturbances and do not influence any other active sensors.

The functional units and signal lines are equipped with devices and measures which shield the physiological signals and image signals and the signal processing and signal editing from the magnetic filters of the transmit antennas. To this end the shell of the catheter is coated with a thin film layer made of conductive nanoparticles. Likewise nanoparticles can be used to effect a magnetic shielding.

The catheter shell is provided with a coating which reduces the frictional resistance during guidance through the vessel. This coating can also be based on nanotechnology or alternatively can be made from a silicon material.

To improve the imaging by the IVUS sensor by using ultrasound contrast means the contrast means is introduced directly into the vessel to be examined or the body cavity through a channel in the catheter.

A temperature sensor or a pressure sensor can be arranged in the tip of the catheter to monitor the temperature and the pressure in the vessel or the organ to be examined and treated. The temperature sensor, which is accommodated in the tip of the catheter, enables any possible temperature increase arising as a result of friction to be detected.

Figure 3:
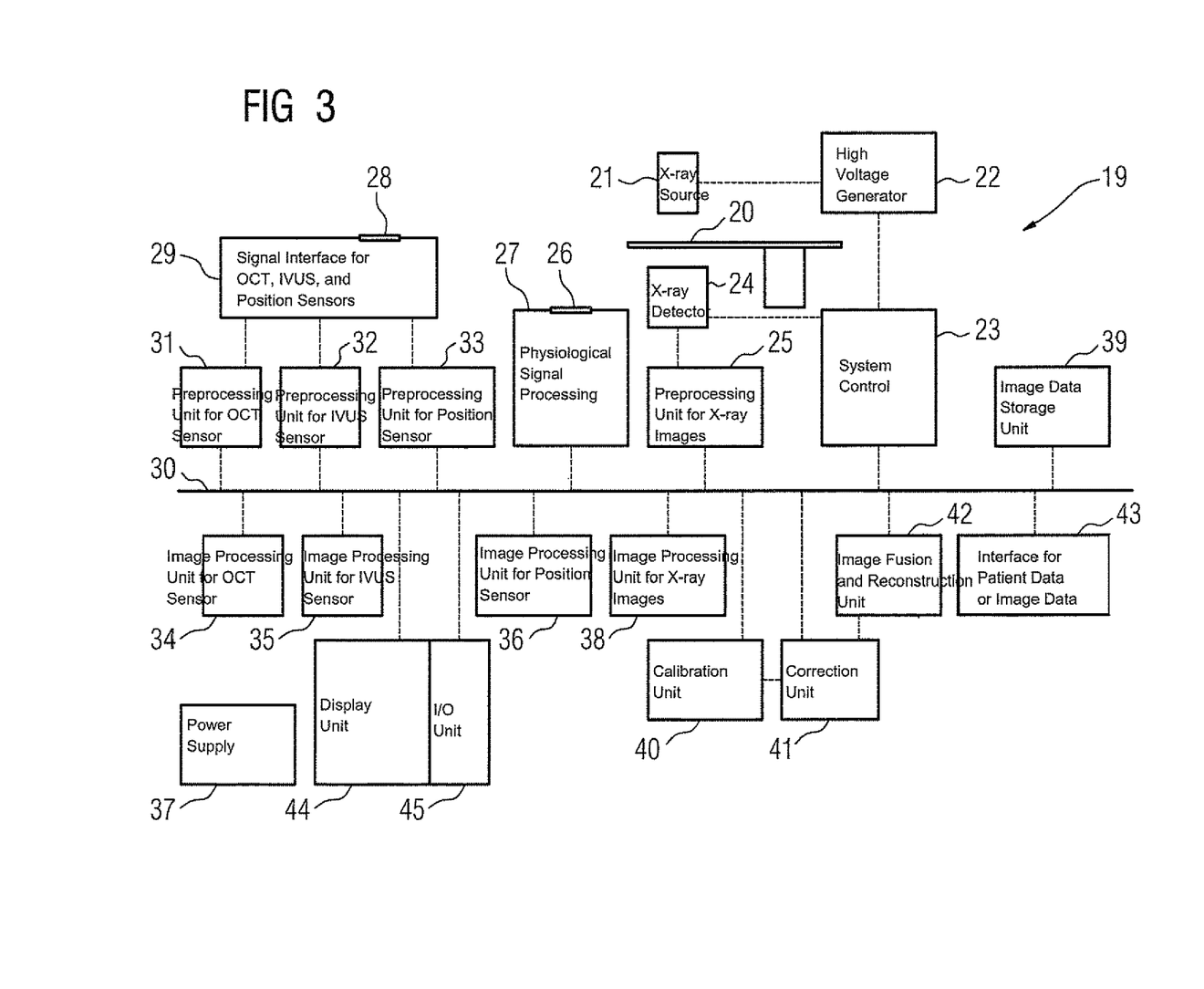

FIG. 3 is a schematic diagram of the inventive treatment unit.

The treatment unit 19 includes a device for carrying out rotablation. For treatment a patient not shown in FIG. 3 is supported on a patient table 20, radiation is emitted by radiation source 21 in the direction of the patient table 20. The radiation is produced via a high-voltage generator 22 controlled via a system control 23. Opposite the x-ray source 21 is arranged an x-ray detector 24 which in its turn is connected to a preprocessing unit 25 for x-ray images. In addition a connection 26 is provided for physiological sensors, which is coupled to a physiological signal processing 27 in order to control ECG signals or pulse signals or the breathing and the blood pressure of a patient.

The actual treatment is undertaken via a connection 28 for the rotablation catheter via a signal interface 29 under image monitoring by OCT, IVUS and the electromagnetic position sensor system. In addition there is a connection to the data bus 30. There are also preprocessing units 31, 32 and 33 provided for OCT, IVUS and the position sensors. Associated image processing units 34, 35 and 36 for OCT, IVUS and the position sensors are also connected to the data bus 30. The power is supplied via a power supply unit 37. Furthermore an image processing unit 38 for the x-ray images is connected to the data bus 30, which features a connection to an image data store 39 for archiving and storing the recorded images. A calibration unit 40 as well as an image correction unit 41 enable interference fields or artifacts of the imaging to be taken into account. The images are fused and reconstructed in an image fusion and/or reconstruction unit 42. In addition there is an interface 43 to a patient data or image data system.

The image data obtained from OCT, IVUS and the position sensor system as well as the x-ray images and possible fusion images of the different imaging techniques are shown on a display unit 44 in two dimensions, three dimensions or four dimensions. The display unit 44 is connected to an input 45 for input by a user.

Figure 4:
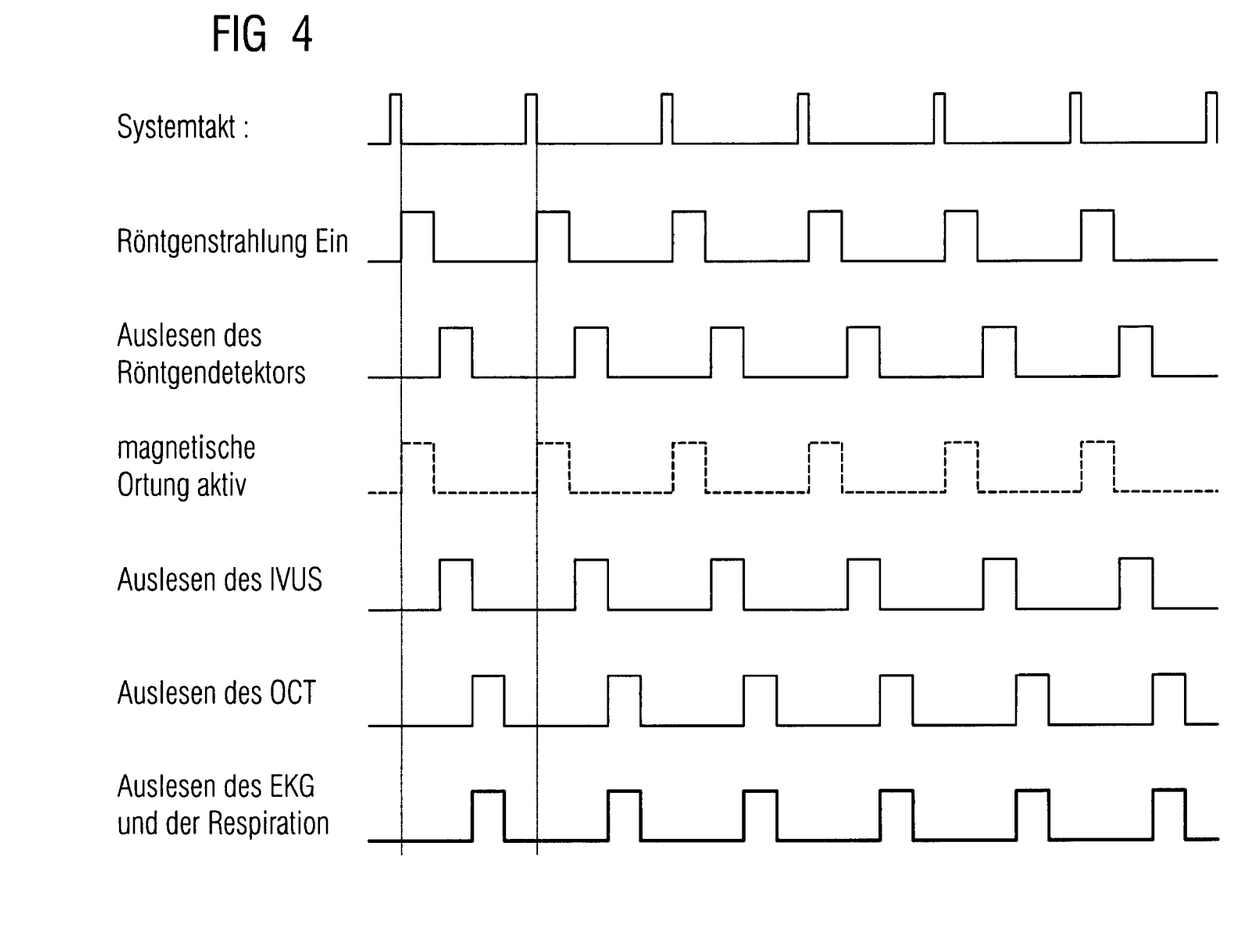

FIG. 4 is a schematic diagram or the sensor read-out of the treatment unit during execution of the inventive method.

A typical execution sequence is as follows: Introducing he catheter under x-ray control, possibly with contrast means, creating the angiographic overview image, creating the images of the position sensors, overlaying the images of the position sensors with the overview angiography by segmentation, registration and image fusion, navigating the catheter based on the images obtained up to the destination position, these steps are in some cases executed in parallel and automatically without the interaction of the user. Once the desired destination position has been reached the flushing fluid for OCT is injected and the stenosis is observed with the OCT-IVUS images in two dimensions or three dimensions at high resolution. During this examination the sensors rotate at a relatively slow speed. Subsequently the OCT-IVUS images are created. Subsequently the OCT-IVUS images are overlaid with the overview angiography by segmentation, registration and image fusion. Subsequently a 3D reconstruction of the OCT-IVUS images is undertaken based on the data of the position sensors. Now the drill head is placed on the catheter tip for carrying out the rotablation. A check is made using OCT-IVUS, in two dimensions and three dimensions, as to whether the position of the drill head is correct. Subsequently the rotablation is carried out using high-frequency rotation of the catheter tip and pushing it slowly forwards through the stenosis in order to cut the plaque away from the vessel wall. Once a specific volume of plaque has been removed this location in the vessel wall is checked with the OCT sensor. The process is repeated until the plaque has been removed at all points. Finally a concluding check is made on the rotablation carried out and the catheter can be pulled out.

The inventive device for carrying out rotablation reduces the method steps required. The OCT sensor delivers good images in the local area, the IVUS sensor sufficiently good images of tissue layers located further down. The electromagnetic position sensors allow 3D images to be created from the OCT and IVUS images. In addition, after an overview angiography has been carried out, by appropriate utilization of the signals of the position sensors, the passage of the catheter can be mapped solely on the basis of the IVUS, OCT and electromagnetic signals, which means that x-ray radiation can be saved. The system delivers important additional medical information about the arteriosclerotic plaque. In addition it allows the correct position of the tip of the catheter to be better checked. A further advantage with the integration of rotablation and OCT also lies in the fact that in this case no separate flushing device must be present for OCT since a flushing means is already used for the drill head.

The sensors of the medical treatment device, which in the exemplary embodiment presented is an x-ray device, are read out partly offset in time and clocked. Initially a system clock is predetermined in which individual system impulses are created, with this pulsed generation being followed by the switching-on of the x-ray radiation and the activation of the magnetic location. After the x-ray radiation is switched off, the x-ray detector readout occurs and at the same time the IVUS data is read out. Subsequently the OCT data is read out, with this occurring at the same time as the readout of the ECG and the data for respiration. This means that the individual sensors are read out or the components of the device are activated in such a way that a mutual fault can be excluded. The time-offset and clocked readout shown here is to be seen as an example for a readout avoiding interference influences.

The invention claimed is:

1. A medical treatment unit for performing a rotablation procedure in a patient, comprising:
   a medical image device which generates an image data of the patient;
   a catheter device integrated with the medical image device comprising:
      a rotablation catheter,
      an OCT sensor arranged in the rotablation catheter,
      an IVUS sensor arranged in the rotablation catheter,
      a position sensor interoperated with the OCT sensor and the IVUS sensor; and
   an image processing unit connected with the OCT sensor, the IVUS sensor, the position sensor, and the medical image device via a data bus, the image processing unit creating a combined image based on the image data from the medical image device and data from the sensors using a section of an image from the OCT sensor to represent a local area and a complementary part of an image from the IVUS sensor to represent a deeper area, producing a combined OCT/IVUS image that is registered computationally with the image data from the medical image device by the image processing unit in a common 3D coordinate system.

2. A method for creating an examination image in a rotablation procedure in a patient, comprising:
   producing an overview X-ray angiography of the patient using an X-ray source, then switching off the X-ray source;
   inserting a rotablation catheter into a body of the patient, the rotablation catheter comprising an OCT sensor, an IVUS sensor and an electromagnetic position sensor;
   processing and combining image data obtained from the OCT sensor, the IVUS sensor the position sensor and the angiography by an image processing unit; and
   creating the examination image based on the processed and combined image data;
   receiving and controlling ECG signals by a signal processor;
   wherein the OCT image data represents examination areas closer to the catheter, and the IVUS image data represents complementary examination areas farther from the catheter; and
   wherein the passage of the catheter is mapped solely on the basis of the IVUS, OCT and position sensor with the X-ray source switched off, saving X-ray radiation;
   wherein a readout of the IVUS image data is non-concurrent with any emission of X-radiation from the X-ray source, and a readout of the OCT image data is non-concurrent with both the emission of X-radiation and the readout of the IVUS image data, and a readout of the ECG signals is non-concurrent with any activation of the electromagnetic position sensor and is concurrent with the readout of the OCT image data;

whereby interference is avoided between the X-ray radiation, IVUS image data, OCT image data, the electromagnetic position sensor activation, and the ECG and respiration data.

3. A device for performing a rotablation in a patient, comprising:
   a rotablation catheter comprising a front end with a drill head;
   an OCT image sensor on the front end of the rotablation catheter;
   an IVUS image sensor on the front end of the rotablation catheter;
   a first electromagnetic position transmitter or sensor on the front end of the rotablation catheter;
   wherein the device for performing rotablation is part of a medical examination unit comprising:
      a 3D medical imaging device external to the patient;
      a second electromagnetic position sensor or transmitter external to the patient;
      a system control;
      a breast band sensor that detects breathing motion characteristics of the patient;
      a data bus that receives data from each of the sensors and from the 3D medical imaging device;
      a functional unit connected to the data bus that removes patient breathing motion artifacts from the position sensor data based on the breast band sensor data; and
      an image fusion unit connected to the data bus;
   wherein the image fusion unit combines images from the OCT and IVUS sensors into a common OCT/IVUS image using a section of an image from the OCT sensor to represent a local area and a complementary part of an image from the IVUS sensor to represent a deeper area, and registers the common OCT/IVUS image with an image from the 3D medical imaging device in a common 3D coordinate system using a 3-dimensional position and orientation of the catheter provided from the position sensor data as corrected for the breathing artifacts; and
   wherein an image display unit on the data bus provides 2D-2D, 2D-3D, 3D-3D, 3D-4D, and 4D-4D overlay images from the medical imaging data and the combined, corrected, and registered image sensor data.

4. The device as claimed in claim 3, wherein the OCT sensor and the IVUS sensor and the first position transmitter or sensor are located within the drill head of the rotablation catheter.

5. The device as claimed in claim 3, wherein the rotablation catheter comprises a permanent magnet or an electromagnet and is controlled by an external magnetic field.

6. The device as claimed in claim 5, wherein:
   the first electromagnetic position transmitter or sensor comprises a transmit coil arranged in the rotablation catheter, and the second electromagnetic position sensor or transmitter comprises an external receiver coil, or
   the second electromagnetic position sensor or transmitter comprises an external transmit coil, and the first electromagnetic position transmitter or sensor comprises a receiver coil arranged in the rotablation catheter.

7. The device as claimed in claim 6, wherein the external receiver coil or the receiver coil arranged in the rotablation catheter comprises an iron core and is functioned as a receiving antenna or an electromagnet for a magnetic navigation.

8. The device as claimed in claim 6, wherein the coils are arranged orthogonally in respective to each other or at a given angle.

9. The device as claimed in claim 3, wherein the OCT sensor or the IVUS sensor is arranged on one side relative to a longitudinal axis of the rotablation catheter.

10. The device as claimed in claim 3, wherein the rotablation catheter is pushed or pulled by a drive unit at a definable speed.

11. The device as claimed in claim 3,
   wherein an image processing unit connected to the data bus approximates a center line or an envelope of a part of a body of the patient to be examined; and
   wherein the OCT and IVUS image data is computationally registered and fused with the image from the 3D medical imaging device based on the approximated center line or envelope, producing a 3D image that is transferred to the common coordinate system.

12. The device as claimed in claim 3, wherein the medical examination unit further comprises a system clock, wherein the 3D medical imaging device comprises an X-ray source and an X-ray detector, and wherein the X-ray detector, the OCT sensor, and the IVUS sensor are read out offset from each other in time to avoid a mutual interference.

13. The device as claimed in claim 3, wherein the rotablation catheter comprises a coating made of conductive nanoparticles to provide shielding from an electromagnetic field.

14. The device as claimed in claim 3, wherein the rotablation catheter and the sensors are electrically decoupled from each other.

15. The device as claimed in claim 3, wherein the rotablation catheter comprises an x-ray marker.

16. The device as claimed in claim 3, wherein the rotablation catheter is coated by a coating to reduce a friction resistance.

17. The device as claimed in claim 3, wherein the rotablation catheter comprises an inflatable balloon to support positioning.

18. The device as claimed in claim 3, wherein the rotablation catheter comprises a temperature sensor or a pressure sensor arranged at a tip area of the rotablation catheter.

19. The device as claimed in claim 3, wherein the 3D medical imaging device provides an overview X-ray angiography, then the X-ray source is switched off and the passage of the catheter is mapped solely on the basis of the IVUS, OCT and the position sensor data, wherein X-ray radiation is saved;
   wherein the medical examination unit further comprises a physiological signal processor that receives and controls ECG signals; and
   wherein a readout of the IVUS image sensor is non-concurrent with any emission of X-radiation from the X-ray source, and a readout of the OCT image sensor is non-concurrent with both the emission of X-radiation and the readout of the IVUS image sensor, and a readout of the ECG signals is non-concurrent with any readout of the position sensor data;
   whereby interference is avoided between the X-ray radiation readout, the IVUS sensor readout, the OCT image sensor readout, the position sensor data readout, and the ECG data readout.

* * * * *